(12) United States Patent
Willnow

(10) Patent No.: US 7,345,018 B2
(45) Date of Patent: Mar. 18, 2008

(54) METHOD OF TREATING SIDE EFFECTS INDUCED BY THERAPEUTIC AGENTS

(75) Inventor: Thomas Willnow, Berlin (DE)

(73) Assignee: Reception ApS, Aarhus C (DK)

( * ) Notice: Subject to any disclaimer, the term of this patent is extended or adjusted under 35 U.S.C. 154(b) by 0 days.

(21) Appl. No.: 10/131,597

(22) Filed: Apr. 25, 2002

(65) Prior Publication Data

US 2003/0202974 A1    Oct. 30, 2003

(51) Int. Cl.
  A61K 31/00    (2006.01)
  A61K 38/00    (2006.01)
  C07K 14/00    (2006.01)
(52) U.S. Cl. ............................ 514/1; 514/2; 424/184.1; 530/300; 530/350
(58) Field of Classification Search ............... 514/1, 514/2, 44; 424/85.1, 130.1, 184.1, 93.1, 424/520, 198.1
See application file for complete search history.

(56) References Cited

U.S. PATENT DOCUMENTS

| | | | |
|---|---|---|---|
| 4,122,171 | A | 10/1978 | Niizato et al. |
| 4,526,888 | A | 7/1985 | Williams et al. |
| 4,554,101 | A | 11/1985 | Hopp .................. 260/112.5 R |
| 4,654,325 | A | 3/1987 | Selenke |
| 5,039,666 | A | 8/1991 | Novick, Jr. |
| 5,059,591 | A | 10/1991 | Janoff et al. |
| 5,079,234 | A | 1/1992 | McGregor et al. |
| 5,087,441 | A | 2/1992 | Elfarra |
| 5,409,704 | A | 4/1995 | Bally et al. |
| 5,731,320 | A | 3/1998 | Wagner et al. |
| 5,773,444 | A | 6/1998 | Ahn et al. |
| 6,130,217 | A | 10/2000 | Arnold et al. |
| 6,177,434 | B1 | 1/2001 | Kopke et al. |
| 6,180,604 | B1 | 1/2001 | Fraser et al. |
| 6,211,234 | B1 | 4/2001 | Astles et al. |
| 6,380,356 | B1 | 4/2002 | Griffin et al. |
| 6,462,194 | B1 | 10/2002 | Winn et al. |
| 6,645,983 | B1 | 11/2003 | Joseph et al. |
| 2002/0132795 | A1 | 9/2002 | Stogniew et al. |

FOREIGN PATENT DOCUMENTS

| | | |
|---|---|---|
| EP | 0 473 145 A1 | 3/1992 |
| EP | 0 483 634 | 5/1992 |
| GB | 1 364 521 | 8/1974 |
| WO | WO 88/04925 A1 | 7/1988 |
| WO | WO 89/05637 | 6/1989 |
| WO | WO 99/02145 | 1/1999 |
| WO | WO 99/37757 A1 | 7/1999 |
| WO | WO 00/57871 A2 | 10/2000 |
| WO | WO 01/05383 A2 | 1/2001 |
| WO | WO 01/12607 | 2/2001 |
| WO | WO 01/87853 A1 | 11/2001 |
| WO | WO 02/053519 | 7/2002 |
| WO | WO 03/066572 | 8/2003 |
| WO | WO-2003/080103 A1 * | 10/2003 |

OTHER PUBLICATIONS

Ilso et al. Megalin and cubilib: synergistic endocytic receptors in renal proximal tubule. Am J Physiol Renal Physiol 280: F562 F573, 2001.*
Nagai et al. Role of megalin in renal handling of aminoglycosides. Am J Physiol Renal Physiol 281: F337-F334, 2001.*
Josepovitz et al. Inhibition of gentamicin uptake in rat renal cortex in vivo by aminoglycosides and organic polycations. J Pharmacol Exp Ther. 223(2):314-321, 1982.*
Forge et al. Aminoglycoside antibiotics. Audiology and Neurootology 5: 3-22, 2000.*
Melman et al. High affinity binding of receptor-associated protein to heparin and low density lipoprotein receptor-related protein requires similar basic amino acid sequence motifs. J Biol Chem 276(31): 29338-29346, 2001.*
Evans et al. Polymyxin B sulfate and colistin: old antibiotics for emerging multiresistant gram-negative bacteria. Annals of Pharmacol 33: 960-967, 1999.*
Ouderkirk et al. Polymyxin B nephrotoxicity and efficacy against Nosocomial infections caused by multiresistant gram-negative bacteria. AntiMicrob Agents Chemotherapy 47(8): 2659-2662, 2003.*
Williams et al. Inhibition of renal membrane binding and nephrotoxicity of aminoglycosides. J Pharmacol Exp Therap 237(3): 919925, 1986.*
Watanabe et al. Targeted prevention of renal accumulation and toxicity of gentamicin by aminoglycoside binding receptor antagonists. J Controlled Release 95: 423-433, 2004.*
Dowling, R.B., and Wilson, R., "*Pseudomonas aeruginosa* Respiratory Infections," *Clin. Pulm. Med.* 6:278-286, Williams & Wilkins (1999).
Begg, E.J. and Barclay, M.L., "Aminoglycosides—50 years on," *Br. J. Clin. Pharmacol.* 39:597-603, Blackwell Science Ltd., (1995).
Burton, M.E. et al., "Comparison of drug dosing methods," *Clin. Pharmacokinetics* 10:1-37, ADIS Press Limited, (1985).
Christensen, E.I. and Willnow, T.E., "Essential role of megalin in renal proximal tubule for vitamin homoestasis," *J. Am. Soc. Nephrol.* 10:2224-2236, American Society of Nephrology, (Oct. 1999).
Decorti, G. et al., "Endocytosis of gentamicin in a proximal tubular renal cell line," *Life Sci.* 65:1115-1124, Elsevier Science, Inc., (Aug. 1999).
Ernfors, P. et al., "Protection of auditory neurons from aminoglycoside toxicity by neurotropin-3," *Nat. Med.*, 2:463-267, Nature Publishing Co., (1996).
Ford, D.M. et al., "Apically and basolaterally internalized anminoglycosides colocalize in LLC-$PK_1$ lysosomes and alter cell function," *Am. J. Physiol.*, 266:C52-57, American Physiological Society, (1994).

(Continued)

Primary Examiner—Bridget E Bunner
(74) Attorney, Agent, or Firm—Iver P. Cooper

(57) ABSTRACT

The invention relates to agents for the prevention of organ damage, in particular of the kidneys and the inner ear, induced by the administration of aminoglycosides. Agents according to the invention are all substances which are megalin and/or cubilin antagonists (inhibitors). In particular, these are molecules (compounds) having polybasic structures which bind to megalin and inhibit the binding of aminoglycosides and related substances.

12 Claims, 6 Drawing Sheets

OTHER PUBLICATIONS

Figure 1:
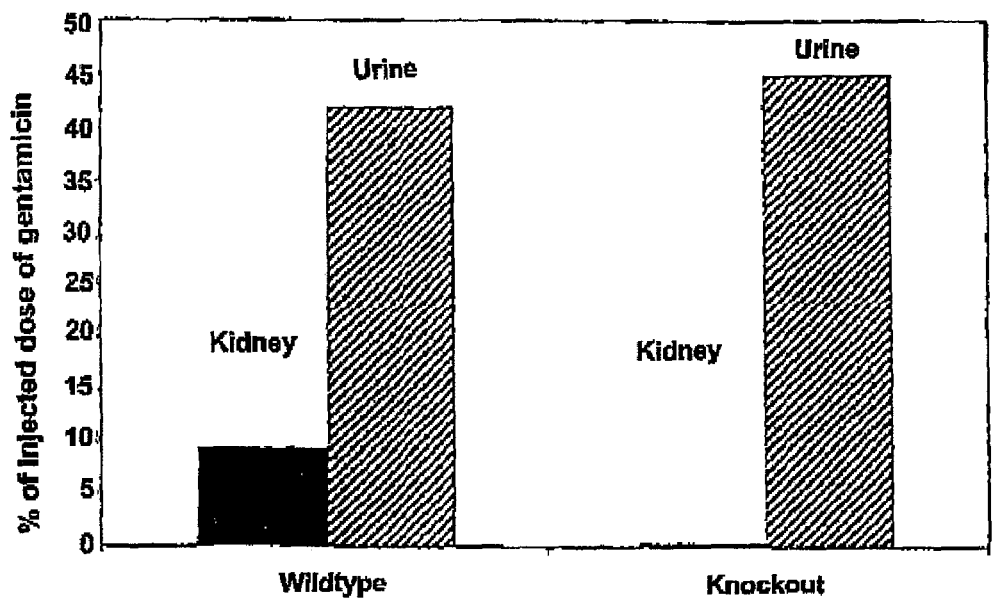

Kyte, J. and Doolittle, R.F., "A simple method for displaying the hydropathic character of a protein," *J. Mol. Biol.*, 157:105-132, Academic Press, Inc. (London) Ltd., (1982).

Lee, S.M. et al., "Nitrendipine protects against animoglycoside nephrotoxicity in the rat," *J. Cardiovasc. Pharmacol.*, 9 (Suppl. 1):S65-S69, Raven Press Books, Ltd., (1987).

Moestrup, S.K. et al., "Evidence that epithelial glycoprotein 330/megalin mediates uptake of polybasic drugs," *J. Clin. Invest.*, 96:1404-1413, The American Society for Clinical Investigation, Inc., (1995).

Nykjaer, A. et al., "An endocytic pathway essential for renal uptake and activation of the steroid 25- (OH) vitamin $D_3$," *Cell*, 96:507-515, Cell Press, (Feb. 1999).

Schacht, J., "Aminoglycoside ototoxicity: prevention in sight?" *Otolaryngol. Head Neck Surg.*, 118:674-677, Mosby Press, (1998).

Schmitz, C. et al., "Megalin deficiency offers protection from renal aminoglycoside accumulation," *J. Biol. Chem.*, 277:618-622, The American Society for Biochemistry and Molecular Biology, Inc., (Jan. 2002).

Willnow, T.E. et al., "Functional expression of low density lipoprotein receptor-related protein is controlled by receptor-associated protein in vivo," *Proc. Natl. Acad. Sci. USA*, 92:4537-4541, National Academy of Sciences, (1995).

Willnow, T.E. et al., "Low density lipoprotein receptor-related protein and gp330 bind similar ligands, including plasminogen activator-inhibitor complexes and lactoferrin, an inhibitor of chylomicron remnant clearance," *J. Biol. Chem.*, 267:26172-26180, The American Society for Biochemistry and Molecular Biology, Inc., (1992).

Willnow, T.E. et al., "Molecular Dissection of ligand binding sites on the low density lipoprotein receptor-related protein," *J. Biol. Chem.*, 269:15827-15832, The American Society for Biochemistry and Molecular Biology, Inc., (1994).

Willnow, T.E. et al., "RAP, a specialized chaperone, prevents ligand-induced ER retention and degredation of LDL receptor-related endocytic receptors," *EMBO J.*, 15:2632-2639, Oxford University Press, (1996).

Xuan, W. et al., "Effects of compound injection of *Pyrola rotundifolia* L and *Astragalus membranaceus* BGE on experimental guinea pigs' gentamycin ototoxicity," *Ann. Otol. Rhinol. Laryngol.*, 104:374-380, Annals Publishing Company, (1995).

Girton, R.A. et al., "Clusterin protects renal tubular epithelial cells from gentamicin-mediated cytotoxicity," *Am. J. Physiol. Renal Physiol.* 282:F709-F709, American Physiological Society, (2002; published online Dec. 4, 2001).

Hjalm, G. et al., "Cloning and sequencing of human gp330, a Ca(2+)-binding receptor with potential intracellular signaling properties," *Eur. J. Biochem.* 239:132-137, Blackwell Science Ltd., (1996).

Genbank Accession No. XM_003315, "*Homo sapiens* low density lipoprotein-related protein-associated protein 1 (alpha-2-macroglobulin receptor-associated protein 1) (LRPAP1), mRNA," Direct submission, National Center for Biotechnology Information, NIH, Bethesda, MD 20894, (Oct. 2001).

Genbank Accession No. XM_011904, "*Homo sapiens* cubilin (intrinsic factor-cobalamin receptor) (CUBN), mRNA," Direct submission, National Center for Biotechnology Information, NIH, Bethesda, MD 20894, (May 2002).

Genbank Accession No. U33837, Hjalm, G. et al., "Human glycoprotein receptor gp330 precursor, mRNA, complete cds,", Jan. 31, 1997.

Edwards, M.L., et al., "Polyamine Analogues with Antitumor Activity," *J. Med. Chem.* 33:1369-1375, American Chemical Society (1990).

Fan, D., et al., "Reversal of multidrug resistance in murine fibrosarcoma cells by thioxanthene flupentixol," *Invest. New Drugs* 12:185-195, Kluwer Academic Publishers (1994).

Heys, S.D., et al., "Potentiation of the response to chemotherapy in patients with breast cancer by dietary supplementation with L-arginine: results of a randomised controlled trial," *Int. J. Oncol.* 12:221-225, Lychnia (1998).

Kondratov, R.V., et al., "Small molecules that dramatically alter multidrug resistance phenotype by modulating the substrate specificity of P-glycoprotein," *Proc. Natl. Acad. Sci. USA* 98:14078-14083, National Academy of Sciences (Nov. 2001).

Lin, P.K.T., and Pavlov, V.A., "The Synthesis and In Vitro Cytotoxic Studies of Novel Bis-naphthalimidopropyl Polyamine Derivatives," *Bioorg. Med. Chem. Lett.* 10:1609-1612, Pergamon Press (2000).

Milam, K.M., et al., "Reduction in cis-Diamminedichloroplatinum(II)-induced Cytotoxicity, Sister Chromatid Exchange, and DNA Interstrand Cross-Links in 9L Cells Treated with the Polyamine Biosynthesis Inhibitor (2R,5R)-6-Heptyne-2,5-diamine," *Cancer Res.* 49:6945-6948, American Association for Cancer Research (1989).

Tomida, A., et al., "Novel Mechanism of N-Solanesyl-N,N'-Bis(3,4-dimethoxybenzyl)ethylenediamine in Potentiation of Antitumor Drug Action on Multidrug-resistant and Sensitive Chinese Hamster Cells," *Jpn. J. Cancer Res.* 82:127-133, Japanese Cancer Association (1991).

Wiebkin, P., et al., "Inhibition of Metabolism-Mediated Cytotoxicity by 1,1-Disubstituted Hydrazines in Mouse Mastocytoma (Line P815) Cells," *Biochem. Pharmacol.* 31:2921-2928, Pergamon Press (1982).

Watanabe, et al., "Targeted prevention of renal accumulation and toxicity of gentamicin by aminoglycoside binding receptor antagonists", *Journal of Controlled Release*, vol. 95, pp. 423-433 (2004).

* cited by examiner

METHOD OF TREATING SIDE EFFECTS INDUCED BY THERAPEUTIC AGENTS

The invention relates to agents for the prevention of organ damage, in particular of the kidneys and the inner ear, induced by the administration of therapeutic agents.

BACKGROUND

It is known that aminoglycosides are some of the most important antibiotics for the treatment of severe bacterial infections. They are the preferred agents against a number of dram-negative bacteria. Their annual market potential in Germany is about 500 million DM. At present, the market share of the aminoglycosides in the field of anti-infectious agents is even rapidly increasing. This is above all due to the general increase in the occurrence of pathological strain resistance to other classes of antibiotics.

The main obstacle in the clinical use of aminoglycosides is their severe oto- and nephrotoxic side effects which especially lead to complete loss of hearing and to renal failure in the long term. The use of aminoglycosides is thus not only associated with a high risk, but also entails high resulting costs. Their use is therefore restricted to incidences of the most severe infections in the industrial countries. In the developing countries in which aminoglycosides are more often used because of their low production costs, these antibiotics account for 70% of all oases of acquired deafness.

As for the causes of their toxicity, it is so far only known that aminoglycosides bind to the surface of cells in the kidneys and the inner ear and are taken up into the cells through unknown mechanisms. As aminoglycosides are only weakly degradable in the cells, they accumulate in large numbers and lead to destruction of the cell structures and thus to renal damage and loss of hearing. Various surface structures or receptors have been made responsible for the binding and uptake of the antibiotics; however, a clear demonstration of the binding sites of aminoglycosides on the body cells has not yet been possible. Decorti et al. have postulated that the uptake of aminoglycosides is a receptor-independent diffusion process (Decorti et al. 1999, *Life Sciences* 65, 1115-1124). On the other hand, Moestrup et al. were of the opinion that megalin, a surface receptor of the kidneys, is responsible for the uptake of antibiotics (Moestrup et al., *J. Clin. Invest.* 96, 1404-1413, 1995). However, Moestrup et al. could only show the binding of aminoglycosides to megalin in test tubes and in cultivated cells. On the contrary, in an animal model, the use of receptor antagonists did not lead to any significant inhibition of the aminoglycoside uptake into the kidneys. Moreover, the aminoglycosides also bind to other surface receptors (so-called LRP's) found in the liver, but not in the kidneys. However, as aminoglycosides are only taken up into the organism in the kidneys and in the inner ear, the value of these in vitro experiments is unclear.

Schmitz et al. has shown that megalin deficiency offers protection from renal aminoglycoside accumulation however no effective way for inhibition of aminoglycoside accumulation in megalin sufficient individuals is discussed or shown (Schmitz, C. et al. *The Journal of Biological Chemistry*, Vol 277, No. 1, Issue of January 4, pp. 618-622, 2002).

Up to now, various strategies have been used in order to reduce the toxic effects of the aminoglycosides. Originally, about 40% of all patients experienced nephro- and ototoxic side effects. As these were directly related to the plasma concentration of the antibiotics, concomitant plasma concentration determinations were introduced to control the concentrations of the antibiotics. Moreover, it was shown that administration with intervals of 12 or 24 hours is accompanied by fewer side effects than dosage regimens with a more frequent administration. By such measures, the number of patients with side effects could be reduced to 10% (Burton, M. E., Vasko, M. R. & Brater, D. C. *Clin. Pharmacokinetics* 10, 1-37 (1985)). However, they led to an increase in the treatment costs. These include the laboratory work for plasma concentration determinations (DM 200-600 for a treatment time of 10 days), further resources for medical staff and costs of about DM 800 per patient for diagnosis and therapy of renal disease.

In another strategy to prevent toxic effects, novel aminoglycosides having fewer side effects were developed. An example of these is amikacin, a semi-synthetic derivative of kanamycin (Begg, E. J. & Barclay, M. L. *Br. J. Clin. Pharmac.* 39, 597-603, 1995). The use of amikacin reduced the rate of toxicity to 1-4%. However, this use is also connected with a further increase in the therapy costs as amikacin (DM 180 per day) is clearly more expensive than usual gentamioin compositions (DM 35 per day).

In general it is doubtful whether this strategy of changing aminoglycoside has any effect at all, since a direct correlation between bactericidal effect and toxic effect is seen. Accordingly, Moestrup et al. could show that amikacin has an about 5 times poorer binding than gentamicin to megalin (Moestrup et al., 1995). The apparently direct correlation between toxicity and bactericidal properties is illustrated by the example of amikacin. It is true that this antibiotic has a clearly poorer binding to megalin (lower toxicity), but it has to be used in a 10 times higher dosage than usual aminoglycosides (lower bactericidal activity).

As a third attempt to reduce the toxicity associated with aminoglycosides, the Simultaneous administration of the antibiotics and substances such as neutrophin-3 (Ernfors, P., Duan, M. L., ElShamy, W. M. & Canlon, B. *Nat. Med.* 2, 463-467 (1996)), nitrendipine (Lee, S. M., Pattison, M. E. & Michael, U. F. *J. Cardiovasc. Pharmacol.* 9, S65-S69 (1997)), Pyrola rotundifolia (Xuan, W. & Dong, M. *Ann. Otol. Rhinol. Laryngol.* 104, 374-380 (1995)) or antioxidants was tested (Schacht, J. *Head and Neck Surgery* 118, 674-677 (1998)). The exact mechanisms of the effect of these substances are still not clear. So far, none of these uses have been implemented clinically.

Furthermore, Ford et al. have shown that aminoglycosides are taken up into the kidneys both from the circulation and from the renal filtrate. As megalin is only exposed to the renal filtrate, the scientific community assumes that alternative receptors exist (Ford et al., *Am. J. Physiol.* 1994, 266, C52-C57).

A recent article by Girton et al. questions whether the toxicity of aminoglycosides is due to uptake mediated by megalin (Girton R. A. et al (2002) *Am. J. Renal Physiol.*, 282: F703-709).

SUMMARY OF THE INVENTION

Thus, it is an object of the invention to provide substances capable of reducing or inhibiting the accumulation of aminoglycosides as well as other toxic medicaments in cells, in particular in the kidneys and the inner ear and, in order to avoid damage to organs consisting of the cells.

Accordingly, in one aspect the present invention relates to the use of a substance capable of binding to one or more of the following:

1) a megalin receptor, and/or
2) a cubilin receptor, and/or
3) a therapeutic agent, said therapeutic agent being capable of binding to the megalin receptor and/or the cubilin receptor, for the preparation of a medicament for the treatment of side effects of medical treatment with said therapeutic agent in humans.

Cubilin is a receptor colocalizing with megalin, that may facilititate the endocytic process of megalin by sequestering the therapeutic agent on the cellular surface before megalin-mediated internalization of the cubilin-bound ligand.

In another aspect the invention relates to a method for treating side effects caused by a medical treatment with a therapeutic agent, comprising administering an effective amount of a substance, said substance being capable of binding to one or more of the following:

1) a megalin receptor, and/or
2) a cubilin receptor, and/or
3) a therapeutic agent, said therapeutic agent being capable of binding to the megalin receptor and/or the cubilin receptor, to an individual in need thereof.

In a third aspect the invention relates to a combinatorial medicament comprising a substance, said substance being capable of binding to one or more of the following:

1) a megalin receptor, and/or
2) a cubilin receptor, and/or
3) a therapeutic agent, said therapeutic agent being capable of binding to the megalin receptor and/or the cubilin receptor, and said therapeutic agent, wherein said therapeutic agent is capable of causing side effects by intracellular accumulation.

In yet a further aspect the invention relates to a method for evaluating whether megalin is responsible for cell uptake of a test drug, comprising
establishing an animal model, wherein said animal is megalin deficient,
establishing a control animal being megalin sufficient,
administering a labeled test drug to both animals, and
evaluating the amount of labeled test drug in the cells of the animal model and the control animal.

Furthermore, the invention relates to a method for assessing a candidate substance for treating side effects of medical treatment, comprising
immobilising megalin and/or cubilin receptor on a solid support,
applying a labeled test substance to the solid support,
washing said solid support, and
detecting labeled test substance on the solid support.

DRAWINGS

FIG. 1: Megalin is responsible for the uptake of aminoglycosides into the kidneys.

Radioactively labelled aminoglycosides (gentamicin) were injected into 26 normal (wildtype) and into 3 megalin-deficient mice (knockout). After 24 hours, the secretion of the aminoglycosides into the urine and their accumulation in the kidneys were determined. In wildtype mice, about 10% of the administered aminoglycosides are accumulated in the kidneys and 40% are secreted into the urine. In knockout mice, there is no accumulation of the aminoglycosides in the kidneys because of the receptor deficiency; 40% of the antibiotics are secreted into the urine.

Figure 2:
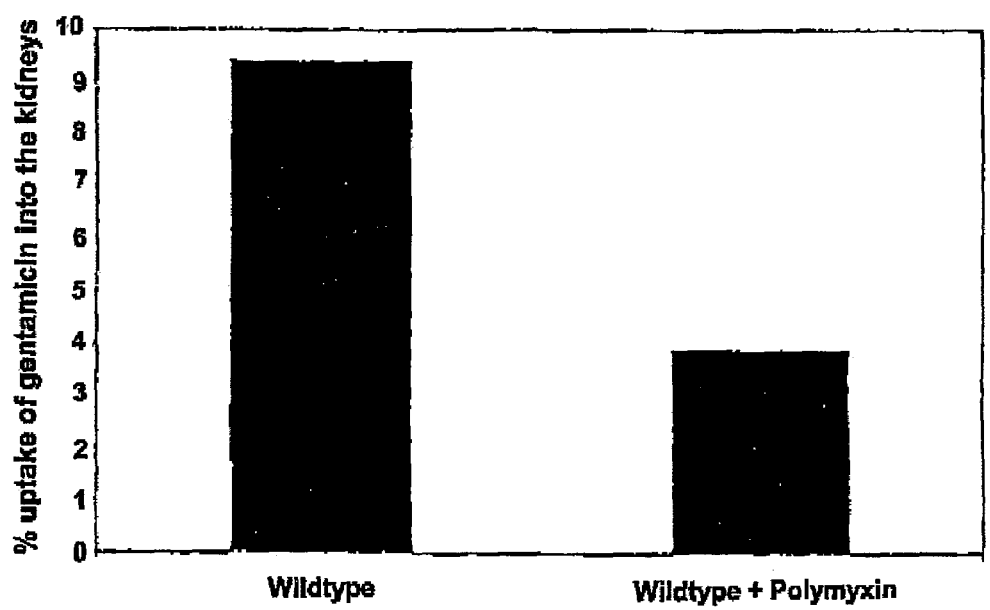

FIG. 2: Megalin antagonists suppress the uptake of aminoglycosides into the kidneys.

Two groups of wildtype mice received an injection of radioactive gentamicin. One group was also injected with polymyxin B, a substance that binds with a high affinity to megalin and displaces gentamicin from the receptor. The administration of polymyxin B reduces the uptake of aminoglycosides into the kidneys by more than 60%.

Figure 3A:
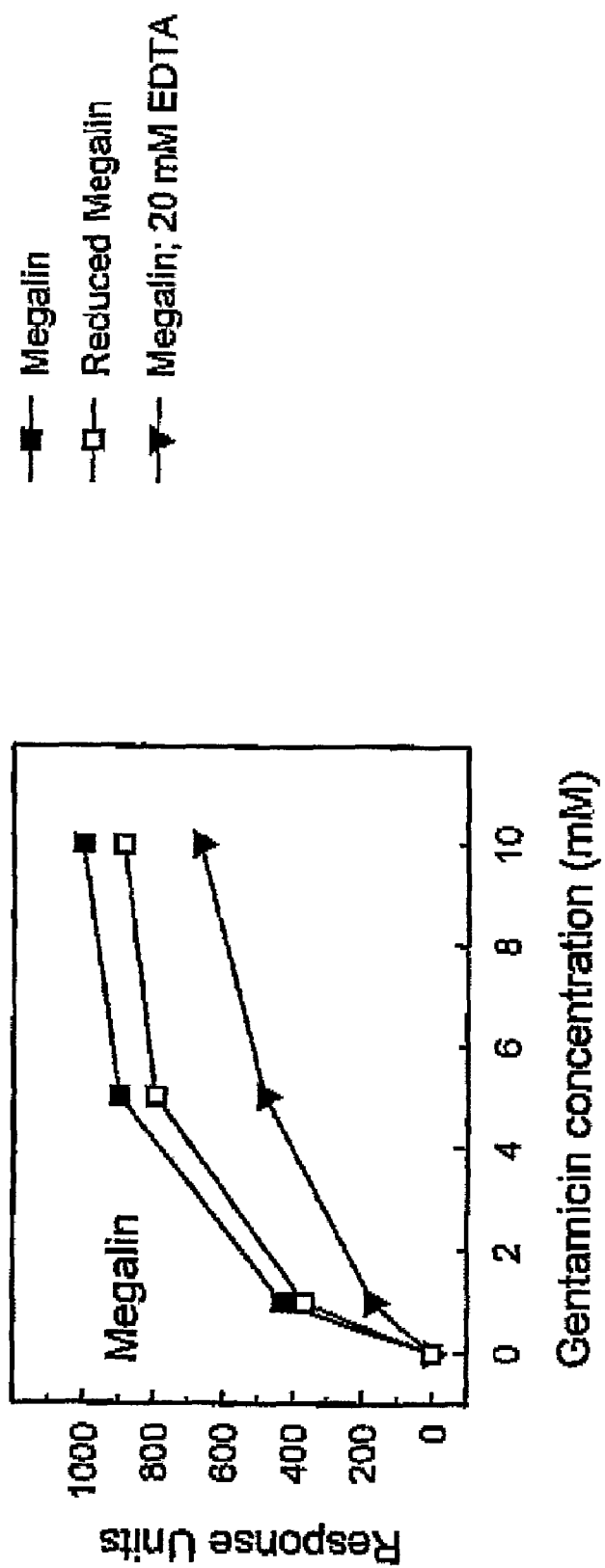
Figure 3B:
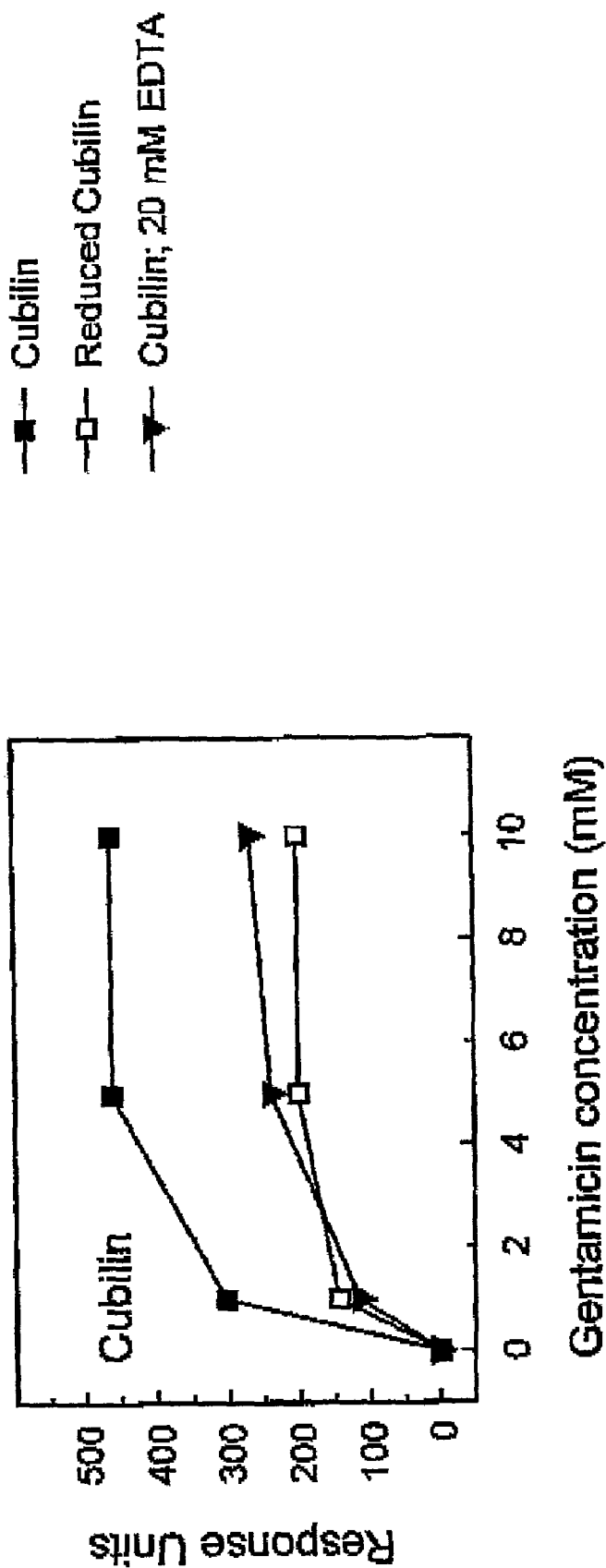
Figure 3C:
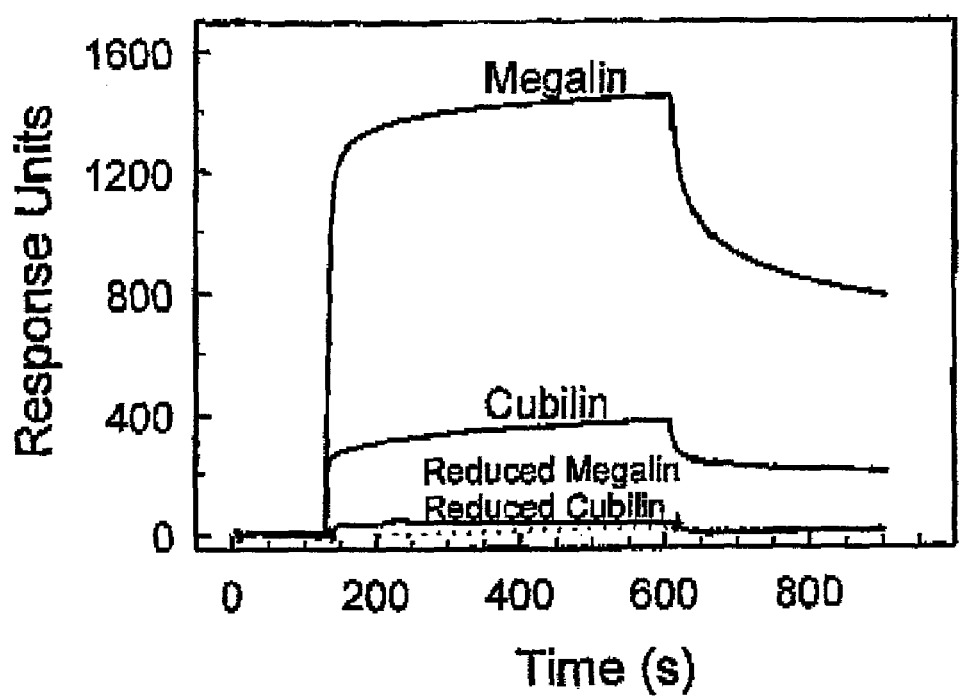

FIG. 3; BIAcore analysis demonstrating direct binding of gentamicin to megalin (panel A) and cubilin (panel B).

Binding to both receptors is not dependent on the native conformation of the receptors, since reduction of disulfide-bridges does not significantly interefere with ligand binding (cubilin may, however, be somewhat more sensitive to the native receptor conformation since reduction affects binding more). Moreover, the addition of EDTA, which depletes the receptors for calcium and affects receptor stability does not abolish binding, indicating that the interaction between receptors and gentamioin may depend on simple ionic interactions rather than the overall confirmation of the receptors. For comparison, binding of RAP (a protein ligand which is basic in structure but known to bind only the native conformation of the receptors) is significantly inhibited when the disulfide-bridges have been disrupted (panel C-dotted line is cubilin in the presence of a reducing agent).

Figure 4:
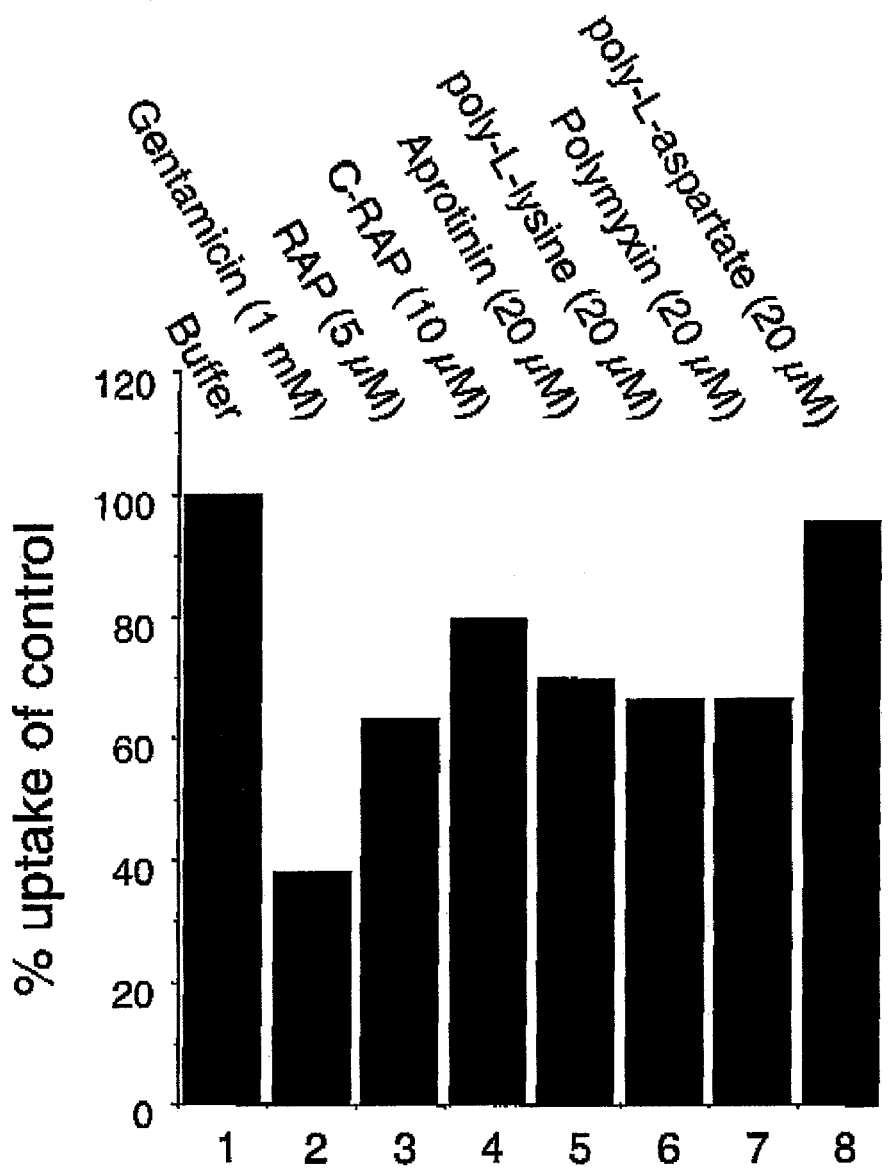

FIG. 4: poly-Lysine inhibits accumulation

To provide further evidence that it may be possible to block binding of drugs to the receptors by basic compounds we have shown that cellular accumulation of radiolabeled gentamicin in cells expressing megalin and cubilin can be inhibited by basic compounds like poly-L-lysine but not by acidic compounds such as poly-L-aspartate. The figure also shows that RAP, although its binding requires a native conformation of the receptors (cf. FIG. 3, panel C) is able to inhibit at least partly the gentamicin binding (C-RAP is the C-terminal domain of RAP). Also, aprotinin and polymyxin B, both basic drugs known to be nephrotoxic inhibit gentamioin uptake.

Figure 5:
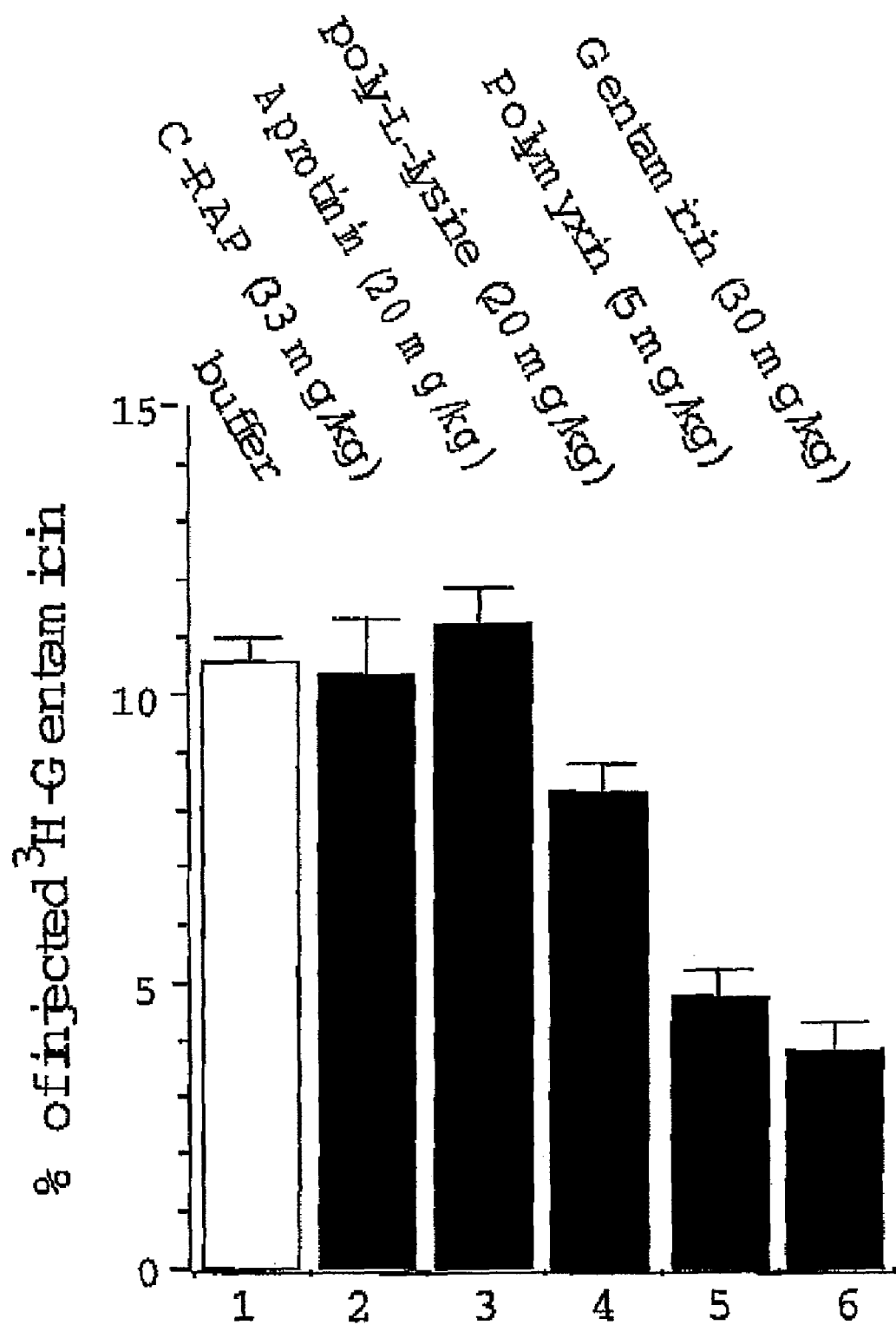

FIG. 5: Inhibition of uptake of radio-labeled gentamicin into mouse kidney

The drugs were administrated intravenously. Uptake of gentamicin can be inhibited by co-infusion with unlabeled gentamicin, polymyxin and poly-lysine. In contrast to the situation in cells, the C-terminal domain of RAP does not inhibit. This is most likely because infused RAP rapidly is cleared from the circulation by uptake into the liver.

DETAILED DESCRIPTION OF THE INVENTION

The principle for the present invention is to reduce the side effects, in particular kidney and inner ear damages, caused by therapeutic agents, possibly due to the accumulation of the therapeutic agent in cells in the organs in question. Thus, the invention is focused on inhibition of the accumulation in the cells of the therapeutic agent. The invention is based on the surprising finding that it could be shown for the first time that contrary to previous hypotheses, only megalin-mediated processes are responsible for the accumulation of the antibiotics in the kidneys when various models for the uptake of aminoglycosides were tested.

Megalin is a 600 kDa endocytosis receptor of the low density lipoprotein (LDL) receptor gene family. Megalin is a multifunctional clearance receptor that binds and internalises a number of macromolecules.

The sequence for the megalin receptor is shown as:
cDNA: U33837
gene: NT_002176

Accordingly, the present invention relates to the use of substances capable of inhibiting the intracellular accumulation. This may for example be done by inhibiting the binding of the therapeutic agent to the megalin receptor by either blocking a sufficient amount of binding sites on the megalin receptor and/or blocking the therapeutic agent so that it maintains the normal therapeutic effect, however is inhibited from binding to the receptor.

Furthermore, the invention relates to inhibiting of the cubilin receptor Cubilin, a 460 kDa membrane-associated protein colocalizing with megalin, may facilititate the endocytic process by sequestering the therapeutic agent on the cellular surface before megalin-mediated internalization of the cubilin-bound ligand. In other words, the therapeutic agent may bind to cubilin as well as directly to megalin. Cubilin, however, appears not to be able to mediate endocytosis on its own but megalin can physically associate with cubilin and mediate its internalization.

The sequence for the cubilin receptor is shown as:
cDNA: XM_011904
gene: NT_008682 (Homo sapiens chromosome 10 working draft sequence segment)

By the present invention classes of substances acting as antagonists have been provided; these classes of antagonists reducing the uptake of aminoglycosides into the organs and thereby suppressing the side effects of these antibiotics.

Substance

The substance according to the invention is capable of binding to either one or both of the receptors discussed above and/or to the therapeutic agent in case of binding to the receptor(s) it is of importance that the binding is effective in respect of blocking binding of the therapeutic agent to the receptor. The megalin receptor for example comprises 50-100 binding sites for the therapeutic agent gentamicin, and it is crucial for the effect of the treatment of this invention, that the substance is capable of blocking an effective amount of these binding sites. Prior art has shown that the naturally occurring substance RAP only binds to a minority of the binding sites, and the inhibitory effect of RAP with respect to intracellular accumulation of a therapeutic agent is also too small to have a clinical significance.

The substance according to the invention may bind either the megalin receptor in order to inhibit endocytosis or the cubulin receptor in order to reduce sequestering and thereby inhibit or reduce endocytosis.

The substance is preferably either capable of binding to a sufficiently amount of binding sites on the receptor(s) or binding to the receptor and sterically hindering the binding of the therapeutic agent.

In a preferred embodiment the substance according to the invention is capable of binding to cubilin, thereby inhibiting or reducing binding of the therapeutic agent to cubilin.

Polybasic Charge Distribution

In a preferred embodiment the substance has at least 3 positive charges in solution. By selecting the positive charges within an interval of 3 to 300 is normally possible to block a sufficient number of binding sites on the megalin receptor and/or the cubilin receptor thereby inhibiting uptake of the therapeutic agent, in a preferred embodiment the substance exhibits at least 5 positive charges, such as at least 10 positive charges, such as at least 15 positive charges. It is preferred that the polybasic charge distribution is having the same charge distribution as aminoglycosides.

This is due to the finding that the binding to the receptor(s) is not necessarily dependent of the native conformation of the receptors, since reduction of disulfide-bridges does not significantly interefere with ligand binding. Moreover; the addition of EDTA, which depletes the receptors for calcium and affects receptor stability does not abolish binding, indicating that the interaction between receptors and gentamicin may depend on simple ionic interactions rather than the overall confirmation of the receptors. For comparison, binding of RAP (a protein ligand which is basic in structure but known to bind only the native conformation of the receptors) is significantly inhibited when the disulfide-bridges have been disrupted, vide FIG. 3.

Accordingly, in one embodiment ft is preferred that the substances are polybasic. By the term polybasic is meant substances having at least 5 positive charges in solution.

Examples of substances exhibiting the preferred positive charge distribution, are polymyxin, structurally or functionally related molecules of polymyxin, aprotinin and polylysine, wherein polylysine is a sequence comprising the amino acid lysine, said sequence having at least 5 lysine residues.

Independent on the charge the substance may be selected from organic molecules, peptides, polypeptides, proteins, antibodies, fragments of antibodies, antibody light chains, wherein the functional requirement being that they are able to bind to megalin and/or cubilin and by this binding inhibit the binding and subsequently uptake of the therapeutic agent into the cell presenting the megalin and/or cubilin receptor.

Furthermore the substance is preferably not an immunogenic substance.

Peptides/proteins

In one embodiment the substance is selected from peptides and/or proteins capable of binding the receptor(s) in question.

It is preferred that the peptide/protein has a length to fit into the various binding sites on the receptor(s). Thus, it is preferred that the peptide/protein has at most 104 amino acids, preferably from 20 to 60 amino acids. In particular, they are minimal functional protein domains.

Furthermore, it is preferred that at least a part of said peptide or protein exhibits a positive charge distribution as described above.

In one embodiment the substance is preferably derived from naturally occurring RAP (receptor-associated protein), it is however preferred that the substance is capable of binding at least 25% of the binding sites for the therapeutic agent on the megalin receptor and/or the cubilin receptor. Accordingly, it is preferred that the substance does not consist of full-length RAP.

RAP (receptor-associated protein) is a cellular protein comprising about 300 amino acids, in a preferred embodiment having the sequence shown in: XM_003315, Gene: AH006949, and known to bind to megalin to suppress the interaction of the receptor with ligands (cellular receptor antagonist) (Willnow et al., *EMBO J*. 15, 2632-2639, 1996). It has been possible to isolate minimal domains of RAP (peptides) that carry the minimal functional domains of the receptor binding and inhibition and thus also function as megalin antagonists.

In a preferred embodiment the RAP derived substance is a peptide comprising a minimal functional domain having at most 104 amino acids, preferably from 20 to 60 amino acids. In particular, they are minimal functional protein domains.

These peptides have at the most 104 amino acids, preferably from 20 to 60 amino acids. A preferred domain is amino acid positions 219-323 of RAP.

In another embodiment the peptide/protein is a cubilin fragment, such as a domain capable of associating with the megalin receptor. Accordingly, such a peptide could competitively inhibit the association between the megalin receptor and the therapeutic agent or the cubilin co-receptor.

In one embodiment the peptide comprises or consists of fragments of the cubilin polypeptide sequence. For example such a fragment may comprise amino acid 1 to 50, such as amino acid 25 to 75, for example amino acid 50 to 100, such as amino acid 75 to 125, for example amino acid 100 to 150, such as amino acid 125 to 175, for example amino acid 150 to 200, such as amino acid 175 to 225, for example amino acid 200 to 250, such as amino acid 225 to 275, for example amino acid 250 to 300, such as amino acid 275 to 325, for example amino acid 300 to 350, such as amino acid 325 to 375, for example amino acid 350 to 400, such as amino acid 375 to 425, for example amino acid 400 to 450, such as amino acid 425 to 475, for example amino acid 450 to 500, such as amino acid 475 to 525, for example amino acid 600 to 550, such as amino acid 525 to 575, for example amino acid 550 to 600, such as amino acid 575 to 625, for example amino acid 600 to 650, such as amino acid 625 to 675, for example amino acid 650 to 700, such as amino acid 675 to 725, for example amino acid 700 to 750, such as amino acid 725 to 775, for example amino acid 750 to 800, such as amino acid 775 to 825, for example amino acid 800 to 860, such as amino acid 826 to 875, for example amino acid 850 to 900, such as amino acid 875 to 925, for example amino acid 900 to 950, such as amino acid 925 to 975, for example amino acid 950 to 1000, such as amino acid 975 to 1025, 1000 to 1050, such as amino acid 1025 to 1075, for example amino acid 1050 to 1100, such as amino acid 1075 to 1125, for example amino acid 1100 to 1150, such as amino acid 1125 to 1175, for example amino acid 1150 to 1200, such as amino acid 1175 to 1225, for example amino acid 1200 to 1250, such as amino acid 1225 to 1275, for example amino acid 1250 to 1300, such as amino acid 1275 to 1325, for example amino acid 1300 to 1350, such as amino acid 1325 to 1375, for example amino acid 1350 to 1400, such as amino acid 1375 to 1425, for example amino acid 1400 to 1450, such as amino acid 1425 to 1475, for example amino acid 1450 to 1500, such as amino acid 1475 to 1525, for example amino acid 1500 to 1550, such as amino acid 1525 to 1575, for example amino acid 1550 to 1600, such as amino acid 1575 to 1625, for example amino acid 1600 to 1650, such as amino acid 1625 to 1675, for example amino acid 1650 to 1700, such as amino acid 1675 to 1725, for example amino acid 1700 to 1750, such as amino acid 1725 to 1775, for example amino acid 1750 to 1800, such as amino acid 1775 to 1825, for example amino acid 1800 to 1850, such as amino acid 1825 to 1875, for example amino acid 18650 to 1900, such as amino acid 1875 to 1925, for example amino acid 1900 to 1950, such as amino acid 1925 to 1975, for example amino acid 1950 to 2000, such as amino acid 1975 to 2025, amino acid 2001 to 2050, such as amino acid 2025 to 2075, for example amino acid 2050 to 2100, such as amino acid 2075 to 2125, for example amino acid 2100 to 2150, such as amino acid 2125 to 2175, for example amino acid 2150 to 2200, such as amino acid 2175 to 2225, for example amino acid 2200 to 2250, such as amino acid 2225 to 2275, for example amino acid 2250 to 2300, such as amino acid 2275 to 2325, for example amino acid 2300 to 2350, such as amino acid 2325 to 2375, for example amino acid 2350 to 2400, such as amino acid 2375 to 2425, for example amino acid 2400 to 2450, such as amino acid 2425 to 2475, for example amino acid 2450 to 2500, such as amino acid 2475 to 2525, for example amino acid 2500 to 2550, such as amino acid 2525 to 2575, for example amino acid 2550 to 2600, such as amino acid 2575 to 2625, for example amino acid 2600 to 2650, such as amino acid 2625 to 2675, for example amino acid 650 to 700, such as amino acid 2675 to 2725, for example amino acid 2700 to 2750, such as amino acid 2725 to 2775, for example amino acid 2750 to 2800, such as amino acid 2775 to 2825, for example amino acid 2800 to 2850, such as amino acid 2825 to 2887 of the cubilin polypeptide sequence.

In another embodiment the peptide/protein is a megalin fragment, such as a domain capable of associating with the cubulin receptor. Accordingly, such a peptide could competitively inhibit the association between the megalin receptor and the therapeutic agent or the cubilin co-receptor. Thus, in another embodiment the substance comprise or consists of fragments of the megalin polypeptide sequence. For example such a fragment may comprise amino acid 1 to 50, such as amino acid 25 to 75, for example amino acid 50 to 100, such as amino acid 75 to 125, for example amino acid 100 to 150, such as amino acid 125 to 175, for example amino acid 150 to 200, such as amino acid 175 to 225, for example amino acid 200 to 250, such as amino acid 225 to 275, for example amino acid 250 to 300, such as amino acid 275 to 325, for example amino acid 300 to 350, such as amino acid 325 to 375, for example amino acid 350 to 400, such as amino acid 375 to 425, for example amino acid 400 to 450, such as amino acid 425 to 475, for example amino acid 450 to 500, such as amino acid 475 to 525, for example amino acid 500 to 550, such as amino acid 525 to 575, for example amino acid 550 to 600, such as amino acid 575 to 625, for example amino acid 600 to 650, such as amino acid 625 to 675, for example amino acid 650 to 700, such as amino acid 675 to 725, for example amino acid 700 to 750, such as amino acid 725 to 775, for example amino acid 750 to 800, such as amino acid 775 to 825, for example amino acid 800 to 850, such as amino acid 825 to 875, for example amino acid 850 to 900, such as amino acid 875 to 925, for example amino acid 900 to 950, such as amino acid 925 to 975, for example amino acid 950 to 1000, such as amino acid 975 to 1025, 1000 to 1050, such as amino acid 1025 to 1075, for example amino acid 1050 to 1100, such as amino acid 1075 to 1125, for example amino acid 1100 to 1150, such as amino acid 1125 to 1175, for example amino acid 1150 to 1200, such as amino acid 1175 to 1225, for example amino acid 1200 to 1250, such as amino acid 1225 to 1275, for example amino acid 1250 to 1300, such as amino acid 1275 to 1325, for example amino acid 1300 to 1350, such as amino acid 1325 to 1375, for example amino acid 1350 to 1400, such as amino acid 1375 to 1425, for example amino acid 1400 to 1450, such as amino acid 1425 to 1475, for example amino acid 1450 to 1500, such as amino acid 1475 to 1525, for example amino acid 1500 to 1550, such as amino acid 1525 to 1575, for example amino acid 1550 to 1600, such as amino acid 1575 to 1625, for example amino acid 1600 to 1650, such as amino acid 1625 to 1675, for example amino acid 1650 to 1700, such as amino acid 1675 to 1725, for example amino acid 1700 to 1750, such as amino acid 1725 to 1775, for example amino acid 1750 to 1800, such as amino acid 1775 to 1825, for example amino acid 1800 to 1850, such as amino acid 1825 to 1875, for example amino acid 1850 to 1900, such as amino acid 1875 to 1925, for example amino acid 1900 to 1950, such as amino acid 1925 to 1975, for example amino acid 1950 to 2000, such as amino acid 1975 to 2025, amino acid 2001 to 2050, such as amino acid 2025 to 2075, for example amino acid 2050 to 2100, such as amino acid 2075 to 2195, for example amino acid 2100 to 2150, such as amino acid 2125 to 2175, for example amino acid 2150 to 2200, such as amino acid 2175 to 2225, for example amino acid 2200 to 2250, such as amino acid 2225 to 2275, for example amino acid 2250 to 2300, such as amino acid 2275 to 2325, for example amino acid 2300 to 2360, such as amino acid 2325 to 2375, for example amino acid 2350 to 2400, such as amino acid 2375 to 2425, for example amino acid 2400 to 2450, such as amino acid 2425 to 2475, for example amino acid 2450 to 2500, such as amino acid 2475 to 2525, for example amino acid 2500 to 2550, such as amino acid 2525 to 2575, for example amino acid 2550 to 2600, such as amino acid 2575 to 2625, for example amino acid 2600 to 2650, such as amino acid 2625 to 2675, for example amino acid 2650 to 2700, such as amino acid 2675 to 2725, for example amino acid 2700 to 2750, such as amino acid 2725 to 2775, for example amino acid 2750 to 2800, such as amino acid 2775 to 2825, for example amino acid 2800 to 2850, such as amino acid 2825 to 2875, for example amino acid 2850 to 2900, such as amino acid 2875 to 2925, for example amino acid 2000 to 2950, such as amino acid 2925 to 2975, for example amino acid 2950 to 3000, such as amino acid 2975 to 3025, amino acid 3001 to 3050, such as amino acid 3025 to 3075, for example amino acid 3050 to 3100, such as amino acid 3075 to 3125, for example amino acid 3100 to 3150, such as amino acid 3125 to 3175, for example amino acid 3150 to 3200, such as amino acid 3175 to 3225, for example amino acid 3200 to 3250, such as amino acid 3225 to 3275, for example amino acid 3250 to 3300, such as amino acid 3275 to 3325, for example amino acid 3300 to 3350, such as amino acid 3325 to 3375, for example amino acid 3350 to 3400, such as amino acid 3375 to 3425, for example amino acid 3400 to 3450, such as amino acid 3425 to 3475, for example amino acid 3450 to 3500, such as amino acid 3475 to 3525, for example amino acid 3500 to 3550, such as amino acid 3525 to 3575, for example amino acid 3550 to 3600, such as amino acid 3575 to 3625, for example amino acid 3600 to 3650, such as amino acid 3625 to 3675, for example amino acid 3650 to 3700, such as amino acid 3675 to 3725, for example amino acid 3700 to 3750, such as amino acid 3725 to 3775, for example amino acid 3750 to 3800, such as amino acid 3775 to 3825, for example amino acid 3800 to 3850, such as amino acid 3825 to 3875, for example amino acid 3850 to 3900, such as amino acid 3875 to 3925, for example amino acid 3900 to 3950, such as amino acid 3925 to 3975, for example amino acid 3950 to 4000, such as amino acid 3975 to 4025, amino acid 4001 to 4050, such as amino acid 4025 to 4075, for example amino acid 4050 to 4100, such as amino acid 4075 to 4125, for example amino acid 4100 to 4150, such as amino acid 4125 to 4175, for example amino acid 4150 to 4200, such as amino acid 4175 to 4225, for example amino acid 4200 to 4260, such as amino acid 4225 to 4275, for example amino acid 4250 to 4300, such as amino acid 4275 to 4325, for example amino acid 4300 to 4350, such as amino acid 4325 to 4375, for example amino acid 4350 to 4400, such as amino acid 4375 to 4425, for example amino acid 4400 to 4450, such as amino acid 4425 to 4475, for example amino acid 4450 to 4500, such as amino acid 4475 to 4525, for example amino acid 4500 to 4550, such as amino acid 4525 to 4575, for example amino acid 4550 to 4600, such as amino acid 4575 to 4625, for example amino acid 4600 to 4655 of the megalin polypeptide sequence.

In yet another embodiment the peptide or protein comprises a high amount of positively charged amino acid residues, in particular a high amount of lysine residue. In a preferred embodiment the peptide is a polylysine sequence comprising substantially only lysine residues. Polylysine sequences according to the invention preferably comprises from 5 to 300 lysine residues, more preferably from 10 to 200 lysine residues.

Of course also functional homologues of the polypeptides of the present invention may be used as the substance. Functional homologues of polypeptides according to the present invention is meant to comprise any polypeptide sequence which is capable of associating with a megalin and/or cubilin receptor and thereby prevents association between the therapeutic agent and the megalin and/or cubilin receptor.

Functional homologues according to the present invention comprise polypeptides with an amino acid sequence, which are sharing at least some homology with the predetermined polypeptide sequences as outlined herein above. For example such polypeptides are at least about 40 percent, such as at least about 50 percent homologous, for example at least about 60 percent homologous, such as at least about 70 percent homologous, for example at least about 75 percent homologous, such as at least about 80 percent homologous, for example at least about 85 percent homologous, such as at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with the predetermined polypeptide sequences as outlined herein above.

The homology between amino acid sequences may be calculated using well known algorithms such as for example any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Functional homologues may comprise an amino acid sequence that comprises at least one substitution of one amino acid for any other amino acid. For example such a substitution may be a conservative amino acid substitution or it may be a non-conservative substitution.

A conservative amino acid substitution is a substitution of one amino acid within a predetermined group of amino acids for another amino acid within the same group, wherein the amino acids within a predetermined groups exhibit similar or substantially similar characteristics. Within the meaning of the term "conservative amino acid substitution" as applied herein, one amino acid may be substituted for another within groups of amino acids characterised by having i) polar side chains (Asp, Glu, Lys, Arg, His, Asn, Gin, Ser, Thr, Tyr, and Cys,)
ii) non-polar side chains (Gly, Ala, Val, Leu, lie, Phe, Trp, Pro, and Met)
iii) aliphatic side chains (Gly, Ala Val, Leu, lie)
iv) cyclic side chains (Phe, Tyr, Trp, His, Pro)
v) aromatic side chains (Phe, Tyr, Trp)
vi) acidic side chains (Asp, Glu)
vii) basic side chains (Lys, Arg, His)
viii) amide side chains (Asn, Gin)
ix) hydroxy side chains (Ser, Thr)
x) sulphor-containing side chains (Cys, Met), and xi) amino acids being monoamino-dicarboxylic acids or monoamine monocarboxylic-monoamidocarboxylic acids (Asp, Glu, Asn, Gin).

Non-conservative substitutions are any other substitutions. A non-conservative substitution leading to the formation of a functional homologue would for example i) differ substantially in hydrophobicity, for example a hydrophobic residue (Val, lie, Leu, Phe or Met) substituted for a hydrophilic residue such as Arg, Lys, Trp or Asn, or a hydrophilic residue such as Thr, Ser, His, Gin, Asn, Lys, Asp, Glu or Trp substituted for a hydrophobic residue; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Functional homologues according to the present invention may comprise more than one such substitution, such as e.g. two amino acid substitutions, for example three or four amino acid substitutions, such as five or six amino acid substitutions, for example seven or eight amino acid substitutions, such as from 10 to 15 amino acid substitutions, for example from 15 to 25 amino acid substitution, such as from 25 to 30 amino acid substitutions, for example from 30 to 40 amino acid substitution, such as from 40 to 50 amino acid substitutions, for example from 50 to 75 amino acid substitution, such as from 75 to 100 amino acid substitutions, for example more than 100 amino acid substitutions.

The addition or deletion of an amino acid may be an addition or deletion of from 2 to 5 amino acids, such as from 5 to 10 amino acids, for example from 10 to 20 amino acids, such as from 20 to 50 amino acids. However, additions or deletions of more than 50 amino acids, such as additions from 50 to 200 amino acids, are also comprised within the present invention.

Additional factors may be taken into consideration when determining functional homologues according to the meaning used herein. For example functional homologues may be capable of associating with antisera which are specific for the polypeptides according to the present invention.

In a further embodiment the present invention relates to functional equivalents which comprise substituted amino acids having hydrophilic or hydropathic indices that are within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−9.5); lysine (−3.9); and arginine (−4.5) (Kyle & Doolittle, 1982).

The amino acid hydrophilicity values are: arginine (+3.0); lysine (+3.0); aspartate (+3.0.+−0.1); glutamate (+3.0.+−0.1) serine (+0.3); asparagine (+0.2); glutamine (+0.2glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

Substitution of amino acids can therefore in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition, to the polypeptide compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxy side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with Met-Leu-Phe. Derivatives of the acyl groups are selected from the group of alkylmoieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

The peptides, polypeptides and proteins according to the invention may be produced by any suitable method known to the person skilled in the art, such as synthetically and recombinant.

Immunoglobulins

In another embodiment the substance according to the invention relates to an antibody or an antibody fragment directed to the megalin receptor or the cubilin receptor or to parts of the receptor(s). The antibody fragments are for example IgG light chains or any other IgG fragment. In particular IgG light chains may bind unspecifically to the cubilin receptor, and therefore in relation to binding to the cubilin receptor it is preferred that the substance is a IgG light chain.

Use of the substances according to the invention, especially the polybasic molecules, leads to a clear reduction of toxic side effects of the used therapeutic agents, and this entails a better therapeutic safety and substantially broader possible applications of these therapeutic agents. Furthermore, it has been shown that excess therapeutic agent does not accumulate in the organs but are secreted.

The antibodies and antibody fragments according to the invention may be produced by any suitable method known to the person skilled in the art.

Assay

In a further aspect the invention relates to a method for testing the mechanism of side effects of various drugs, by testing the drug in question in an assay using an animal model.

Accordingly, the invention relates to a method for evaluating whether megalin is responsible for cell uptake of a test drug, comprising establishing an animal model, wherein said animal is megalin deficient, establishing a control animal being megalin sufficient, administering a labeled test drug to both animals, and evaluating the amount of labeled test drug in the cells of the animal model and the control animal.

In one embodiment the animal model is a mouse model with an induced megalin gene defect (knockout mouse; Nykjaer, A. et al., *Cell* 96, 507-515). In these animals, the contribution of megalin and other receptor-mediated or receptor-independent processes to the drug uptake into the kidneys may be tested. The amount of intracellular accumulation of the drug in question as compared to a control having sufficient megalin indicates whether the mechanism of side effects is intracellular accumulation through megalin binding or some other mechanism.

In another aspect of the invention the animal model is a mouse model with an induced RAP gene defect (knockout mouse; Willnow T. E. et al (1995) *Proc. Natl. Acad. Sci.* 92:4537-4541). The RAP knock out mouse is a 50% deficient mouse with respect to megalin, thus capable of uptaking only 50% of the therapeutic agent as compared to the megalin sufficient mouse.

In these animals, the contribution of megalin and other receptor-mediated or receptor-independent processes to the drug uptake into the kidneys may be quantified. The amount of intracellular accumulation of the drug in question as compared to a control having sufficient megalin indicates whether the mechanism of side effects is intracellular accumulation through megalin binding or some other mechanism.

The two animal models may also be combined.

In yet a further aspect the invention relates to a method for assessing a candidate substance for treating side effects of medical treatment, comprising immobilising megalin and/or cubilin receptor on a solid support, applying a labeled test substance to the solid support, washing said solid support, and detecting labeled test substance on the solid support.

The method may for example be used for screening the substance in question in an assay as described below.

The substance according to the invention is preferably a substance capable of inhibiting uptake of labeled (e.g. by biotinylation) drugs, for examples aminoglycosides, such as gentamicin and/or kanamycin in the following ELISA-plate assay:

Megalin and cubilin purified from rabbit kidney cortex is immobilized in wells on microtiter plate or a similar matrix and incubated with the labeled drug of interest alone or in the presence of a putative antagonist substance. Inhibition of drug binding is visualized by for example an enzymatic reaction.

In a preferred embodiment the uptake in this ELISA-plate assay is inhibited by at least 25% as compared to the control, such as at least 30% as compared to the control, such as at least 40% as compared to the control, such as at least 50% as compared to the control, such as at least 60% as compared to the control, such as at least 70% as compared to the control, such as at least 80% as compared to the control, such as at least 90% as compared to the control, Therapeutic Agent The therapeutic agent according to the invention may be any therapeutic agent capable of causing organ damages due to intracellular accumulation in cells in the organs. In particular the therapeutic agent is capable of accumulating in cells in the kidneys and/or inner ear, thus causing kidney damages as well as damages to the inner ear.

In particular the therapeutic agent is selected from aminoglycosides, such as gentamicin and kanamycin, cisplatin, amphotericin B, ifosfomide, polymyxin B, cyclophosphomide, methotrexate, aprotinin and valproate. In a preferred embodiment the therapeutic agent is an aminoglycoside, such as gentamicin and kanamycin.

Also fusion proteins or fusion products used for medical treatment wherein one of the proteins is capable of binding the megalin or the cubilin receptor and the other protein/product cell toxic when accumulating in the cells. In particular fusion products, wherein one part of the product is an antibody or IgG light chain, both capable of unspecifically binding to cubilin, and the other part of the product being cytotoxic, such as cancer treatment, may be co-administered with a substance according to the present invention, in order to reduce organ damage, in particular kidney damage.

Affinity

As shown in the prior art (Moestrup et al. and Schmitz et al.) merely allowing binding of a substance to the megalin receptor does not necessarily cause significant reduction of intracellular accumulation of the therapeutic agent. The substance according to the invention preferably has at least 2 times greater affinity to the megalin receptor and/or the cubilin receptor than the therapeutic agent, in a preferred embodiment at least 5 times greater affinity, in a more preferred embodiment at least 10 times greater affinity, wherein affinity is measured by standard methods in the art.

Dosages

The dosage of the substance according to the invention is depending on the substance in question, however the amount of substance is also closely related to the therapeutic agent co-administered with the substance as well as the dosage of said therapeutic agent.

For all methods of use disclosed herein for the compounds, the daily oral dosage regimen will preferably be from about 0.01 to about 80 mg/kg of total body weight. The daily parenteral dosage regimen about 0.001 to about 80 mg/kg of total body weight.

The term "unit dosage form" as used herein refers to physically discrete units suitable as unitary dosages for human and animal individuals, each unit containing a predetermined quantity of a compound, alone or in combination with other agents, calculated in an amount sufficient to produce the desired effect in association with a pharmaceutically acceptable diluent, carrier, or vehicle. The specifications for the unit dosage forms of the present invention depend on the particular compound or compounds employed and the effect to be achieved, as well as the pharmacodynamics associated with each compound in the host. The dose administered should be an "effective amount" or an amount necessary to achieve an "effective level" in the individual patient.

Since the "effective level" is used as the preferred endpoint for dosing, the actual dose and schedule can vary, depending on inter-individual differences in pharmacokinetics, drug distribution, and metabolism. The "effective level" can be defined, for example, as the blood or tissue level desired in the individual that corresponds to a concentration of one or more compounds according to the invention. Also, the effective level is depending on the therapeutic agent in question, and in particular on the concentration of the effective level in question.

Accordingly, in a preferred embodiment the ratio of the substance administered to the therapeutic agent administered is in the interval of from 200:1 mol:mol to 1:200 mol:mol, such as in the interval of from 100:1 mol:mol to 1:50 mol:mol, such as in the interval of from 50:1 mol:mol to 1:25 mol:mol The substance may be administered in any suitable dosage regime, but is preferably administered with the same intervals as the therapeutic agent, preferably either shortly before or during administration of the therapeutic agent.

Most of the therapeutic agents according to this invention are administered parenterally, often intravenously. The substance according to the invention may be administered in any suitable manner according to the formulation thereof it is however often preferred that the substance is administered parenterally, such as intravenously as the therapeutic agent.

Pharmaceutical Composition

The present invention further relates to a combinatorial medicament comprising the substance according to the invention in combination with the therapeutic agent. Thus, in another aspect the invention relates to a combinatorial medicament comprising a substance, said substance being capable of binding to one or more of the following:

1) a megalin receptor, and/or
2) a cubilin receptor, and/or
3) a therapeutic agent said therapeutic agent being capable of binding to the megalin receptor and/or the cubilin receptor, and said therapeutic agent, wherein said therapeutic agent is capable of causing side effects by intracellular accumulation.

The substance and the therapeutic agent may be administered simultaneously, either as separate formulations or combined in a unit dosage form, or administered sequentially. The combinatorial medicament may be formulated by co-formulating the substance according to the invention with the therapeutic agent for simultaneous administration. In another embodiment the combinatorial medicament is formulated as two separate medicament for either simultaneous or sequential administration.

The main routes of drug delivery according to the present invention are intravenous, oral, and topical, as will be described below, Other drug-administration methods, such as subcutaneous injection, which are effective to deliver the drug to a target site or to introduce the drug into the bloodstream, are also contemplated.

The mucosal membrane to which the pharmacutical preparation of the invention is administered may be any mucosal membrane of the mammal to which the biologically active substance is to be given, e.g. in the nose, vagina, eye, mouth, genital tract, lungs, gastrointestinal tract, or rectum.

In the present context the term compound is used to synonymously with the word substance. Compounds of the invention may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. The compounds may also be administered by inhalation, that is by intranasal and oral inhalation administration.

The compounds according to the invention may be administered with at least one other compound. The compounds may be administered simultaneously, either as separate formulations or combined in a unit dosage form, or administered sequentially. The combinatorial medicament may be formulated by co-formulating the substance according to the invention with the therapeutic agent for simultaneous administration. In another embodiment the combinatorial medicament is formulated as two separate medicament for either simultaneous or sequential administration.

Pharmaceutical compositions containing a compound of the present invention may be prepared by conventional techniques, e.g. as described in Remington: The Science and Practice of Pharmacy 1995, edited by E. W. Martin, Mack Publishing Company, 19th edition, Easton, Pa. The compositions may appear in conventional forms, for example capsules, tablets, aerosols, solutions, suspensions or topical applications.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilising and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The parenteral formulations typically will contain from about 0.5 to about 25% by weight of the active ingredient in solution. Preservatives and buffers may be used. In order to minimise or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The invention claimed is:

1. A method for reducing the accumulation of an aminoglycoside in kidney cells of a human subject in need of such reduction, and thereby reducing kidney damage attributable to said accumulation, said method comprising administering to said individual, before, during or after administration of the aminoglycoside, an aminoglycoside accumulation-reducing effective amount of a substance, which substance is not itself an aminoglycoside, said substance being basic and having an amino group, and being capable of binding to a megalin receptor in kidney cells and inhibiting binding of said aminoglycoside to said receptor, said administration of the substance being at a time such that the substance competes with the aminoglycoside for said receptor, said method resulting in less kidney damage to the subject, as a result of administration of the aminoglycoside and the substance together, as compared to the administration of the same amount of the aminoglycoside alone.

2. The method according to claim 1, wherein said substance has a polybasic charge distribution.

3. The method according to claim 1, wherein said substance in solution has at least 3 positive charges.

4. The method according to claim 1, wherein said substance is selected from a peptide and a protein.

5. The method according to claim 4, wherein said substance is said peptide, and wherein said peptide is a fragment of naturally occurring RAP (receptor-associated protein).

6. The method according to claim 5, wherein said substance is capable of binding at least 25% of the binding sites for said aminoglycoside on said receptor megalin.

7. The method according to claim 5, wherein said peptide has at most 104 amino acids.

8. The method according to claim 1, wherein said substance has at least 2 times greater affinity for said receptor megalin than said aminoglycoside has for said receptor megalin.

9. The method according to claim 1, wherein said accumulation of said aminoglycoside is reduced by at least 25%.

10. The method according to claim 1, wherein the ratio of said substance administered to said aminoglycoside administered is at least 200:1 mol:mol to 1:200 mol:mol.

11. A method for reducing the accumulation of an aminoglycoside in inner ear cells of a human subject in need of such reduction, and thereby reducing inner ear damage attributable to such accumulation, wherein said individual is at risk of developing inner ear damage as a result of the accumulation of said aminoglycoside, said method comprising administering to said individual, before, during or after administration of the aminoglycoside, an aminoglycoside accumulation-reducing effective amount of a substance, which substance is not itself an aminoglycoside, said substance being basic and having an amino group, and being capable of binding to a megalin receptor in inner ear cells and inhibiting binding of said aminoglycoside to said receptor, said administration of the substance being at a time such that the substance competes with the aminoglycoside for said receptor, said method resulting in less inner ear damage to the subject, as a result of administration of the aminoglycoside and the substance together, as compared to the administration of the same amount of the aminoglycoside alone.

12. The method of claim 1 in which the substance is polymyxin B.

* * * * *